(12) United States Patent
Kong et al.

(10) Patent No.: US 9,121,054 B2
(45) Date of Patent: Sep. 1, 2015

(54) DETECTION OF NUCLEIC ACID AMPLIFICATION PRODUCTS IN THE PRESENCE OF AN INTERNAL CONTROL SEQUENCE ON AN IMMUNOCHROMATOGRAPHIC STRIP

(75) Inventors: Huimin Kong, Wenham, MA (US); Yanhong Tong, Boxford, MA (US); Wen Tang, Wilmington, MA (US)

(73) Assignee: BioHelix Corporation, Beverly, MA (US)

(*) Notice: Subject to any disclaimer, the term of this patent is extended or adjusted under 35 U.S.C. 154(b) by 1245 days.

(21) Appl. No.: 12/962,202

(22) Filed: Dec. 7, 2010

(65) Prior Publication Data
US 2011/0229887 A1  Sep. 22, 2011

Related U.S. Application Data

(60) Provisional application No. 61/267,639, filed on Dec. 8, 2009.

(51) Int. Cl.
*C12Q 1/68* (2006.01)
*C12P 19/34* (2006.01)

(52) U.S. Cl.
CPC .................. *C12Q 1/6834* (2013.01)

(58) Field of Classification Search
USPC ............................. 435/6.12, 91.2
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 5,066,584 A | 11/1991 | Gyllensten et al. | |
| 5,344,757 A | 9/1994 | Holtke et al. | |
| 5,399,491 A | 3/1995 | Kacian et al. | |
| 5,455,166 A | 10/1995 | Walker | |
| 5,470,723 A | 11/1995 | Walker et al. | |
| 5,494,810 A | 2/1996 | Barany et al. | |
| 5,554,516 A | 9/1996 | Kacian et al. | |
| 5,955,351 A | 9/1999 | Gerdes et al. | |
| 6,312,929 B1 | 11/2001 | McMillan | |
| 7,282,328 B2 | 10/2007 | Kong et al. | |
| 8,431,387 B2 * | 4/2013 | LaBarre et al. | ............ 435/287.2 |
| 2005/0003374 A1 | 1/2005 | Swenson | |
| 2006/0160078 A1 | 7/2006 | Cardy et al. | |
| 2006/0166232 A1 | 7/2006 | Vickery et al. | |
| 2009/0181388 A1 | 7/2009 | You et al. | |
| 2011/0124126 A1 * | 5/2011 | Weber | ............ 436/501 |

OTHER PUBLICATIONS

Goldmeyer et al. (2008) "Identification of *Staphylococcus aureus* and Determination of Methicillin Resistance Directly from Positive Blood Cultures by Isothermal Amplification and a Disposable Detection Device," *J. Clin. Microbiol.* 46:1534-1536.

Kolk et al. (1994) "*Mycobacterium smegmatis* Strain for Detection of *Mycobacterium tuberculosis* by PCR Used as Internal Control for Inhibition of Amplification and for Quantification of Bacteria," *J. Clin. Microbiol.* 32:1354-1356.

* cited by examiner

*Primary Examiner* — Kenneth Horlick
(74) *Attorney, Agent, or Firm* — McDermott Will & Emery LLP

(57) ABSTRACT

Compositions and methods useful in nucleic acid assays are provided. The invention permits detection of test and control nucleic acids. Test nucleic acids can be immobilized at multiple locations, such that amplification of either a test nucleic acid or a control nucleic acid provides a captured nucleic acid in a control capture zone.

8 Claims, 10 Drawing Sheets

Schematic diagram of using Split-Probe to enhance the intensity of the control line.

Figure 1: Schematic diagram of amplification of a target sequence in the presence of an internal control sequence and subsequent detection on a lateral-flow strip.
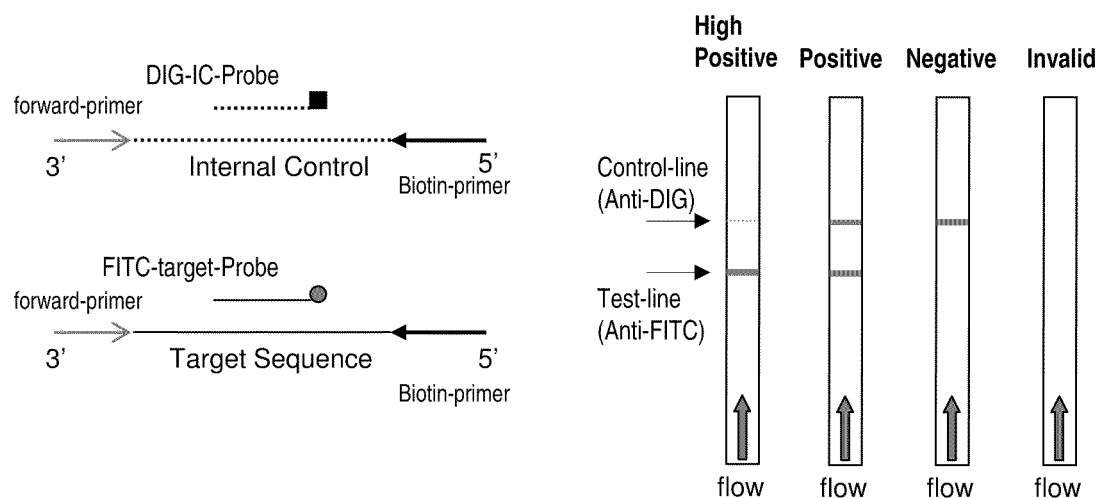

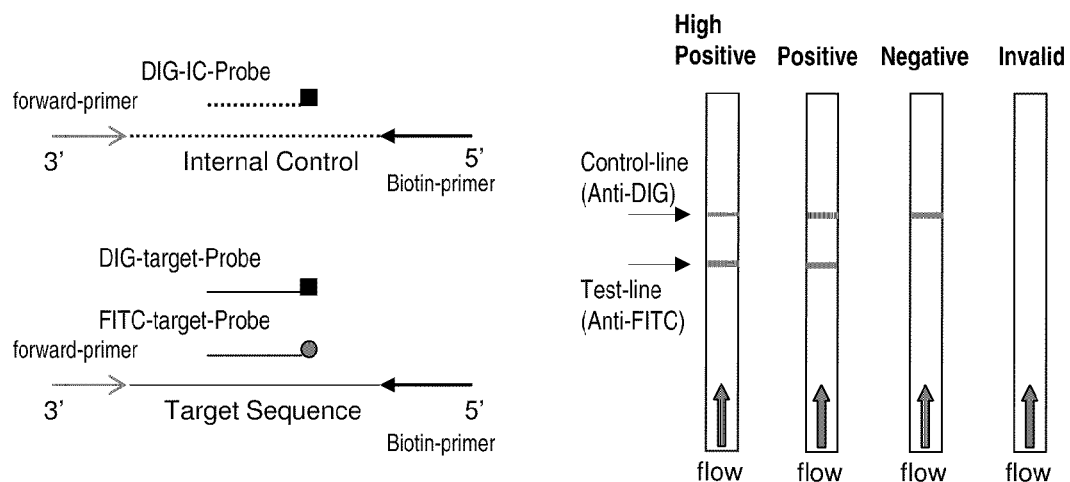
Figure 2. Schematic diagram of using Split-Probe to enhance the intensity of the control line.

Figure 3. Using dual capture zones at the control line to enhance the intensity of that line.
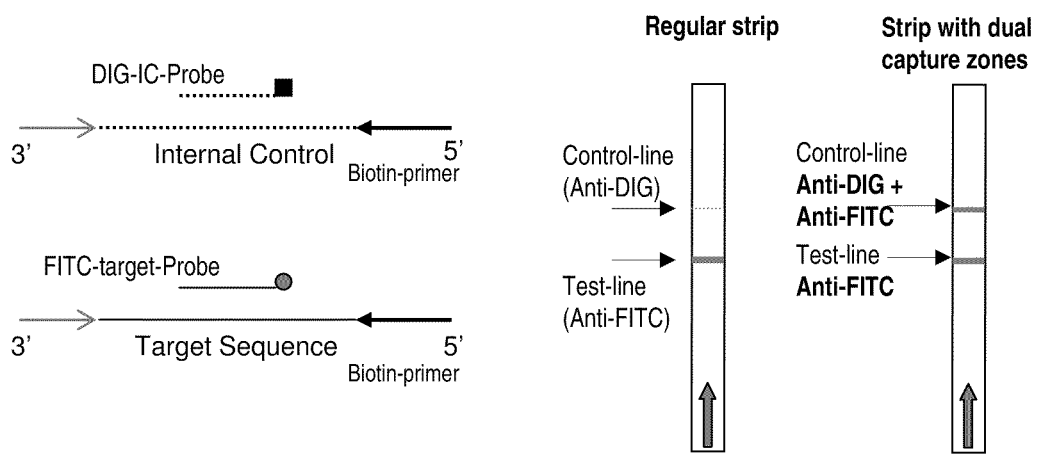

Figure 4. Schematic diagram of internal control using labeled primer.
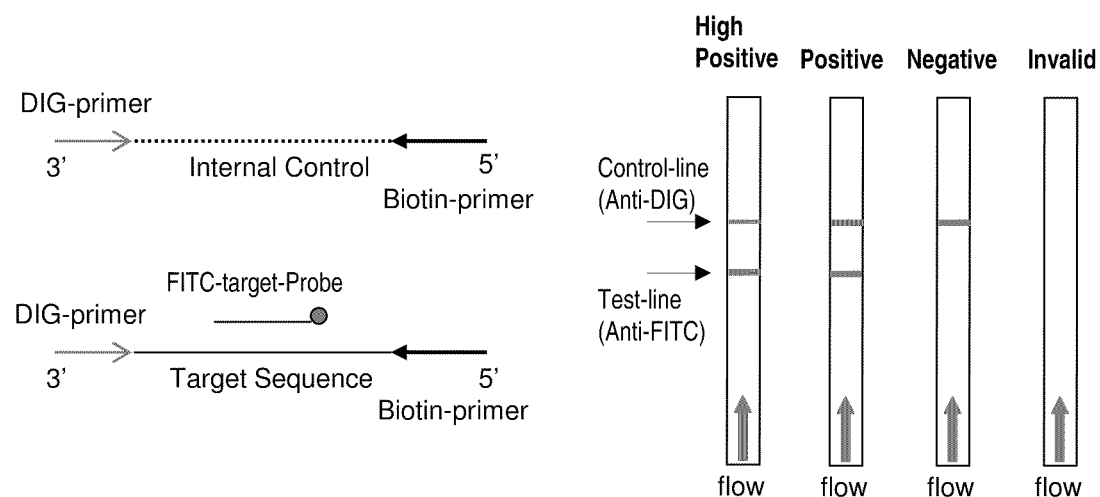

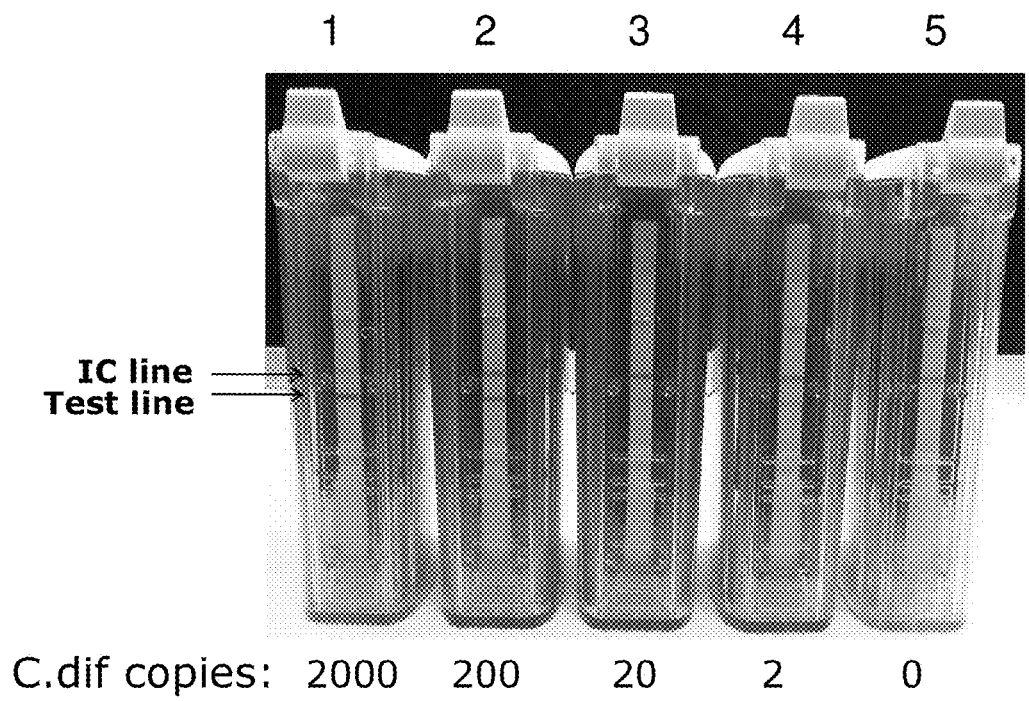
Figure 5: Amplification of a target sequence of *C. difficile* in the presence of an internal control sequence and subsequent detection on lateral flow strips Figure 6: Comparison of amplification / detection between the reactions without split probe (Panel A) and the reactions with split probe (Panel B).
Panel A. Without split probe
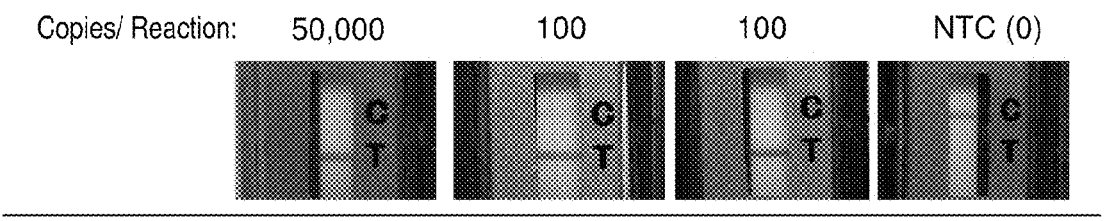
Panel B. With split probe
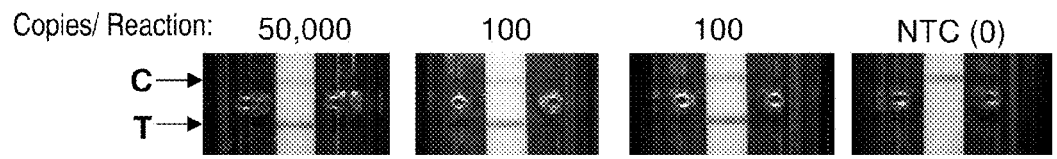

Figure 7, Panel A: Determining the ratio of the split probes: 50,000 target.
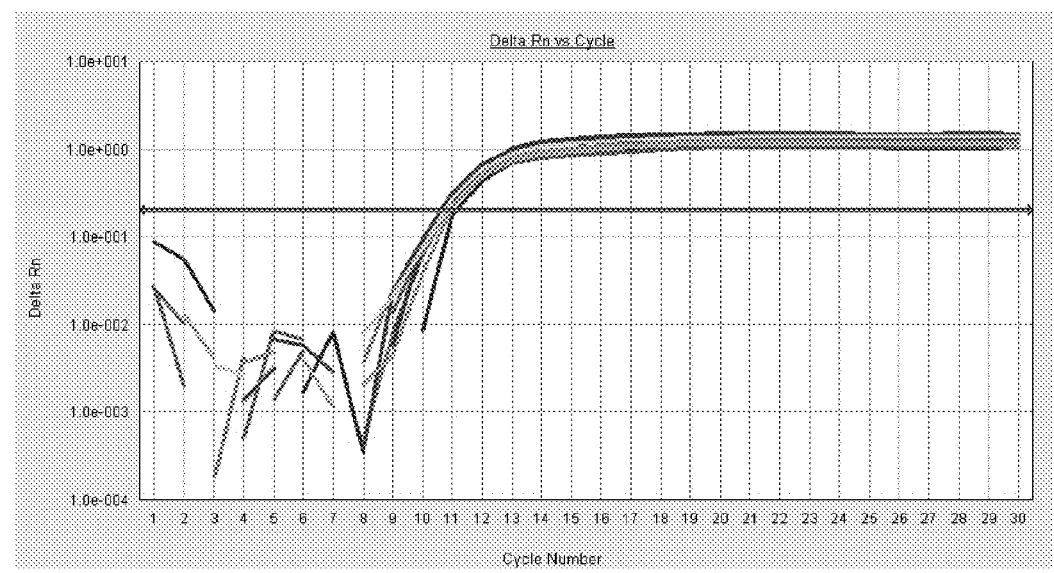
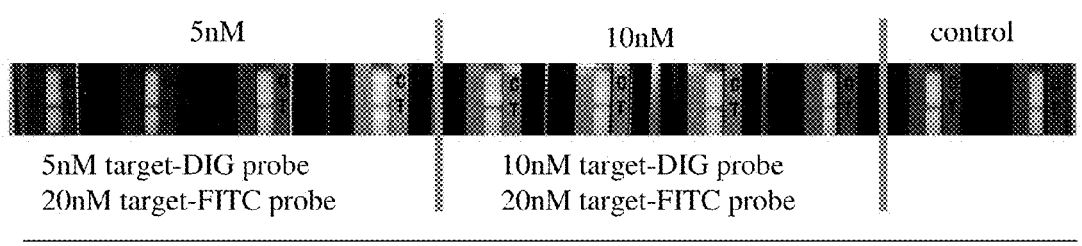
| 5nM | 10nM | control |
|---|---|---|
| 5nM target-DIG probe<br>20nM target-FITC probe | 10nM target-DIG probe<br>20nM target-FITC probe | |

Figure 7, Panel B: Determining the ratio of the split probes: 500 target.
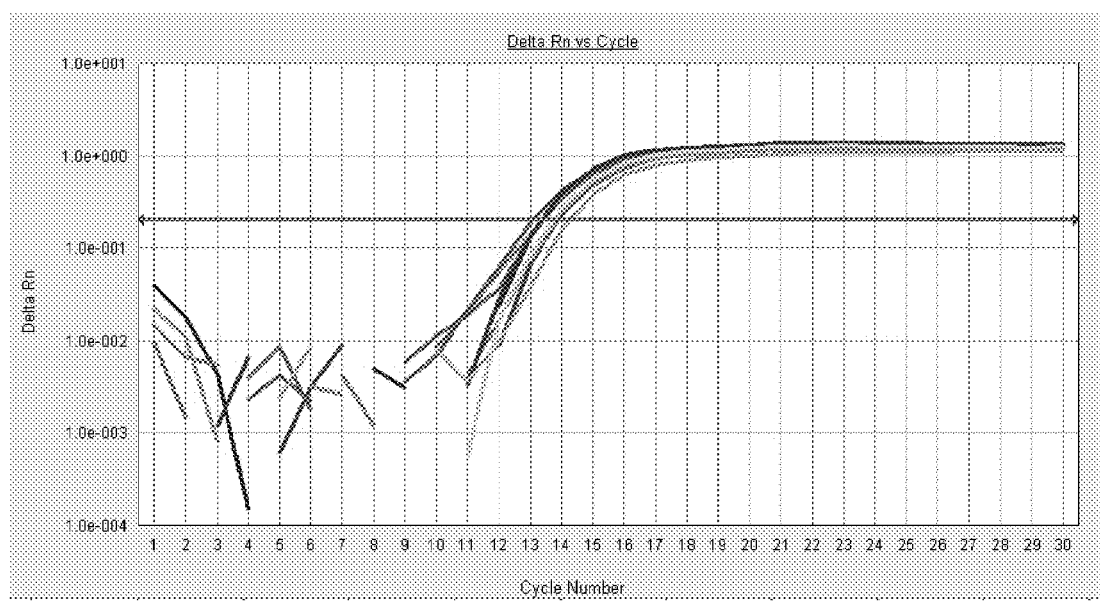
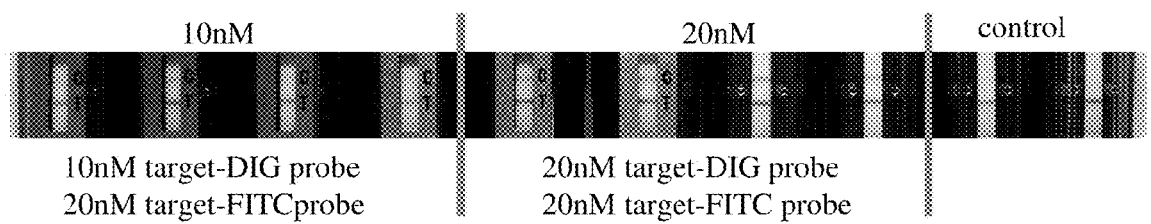
| 10nM | 20nM | control |
|---|---|---|
| 10nM target-DIG probe<br>20nM target-FITCprobe | 20nM target-DIG probe<br>20nM target-FITC probe | |

Figure 8: Detection of *Clostridium difficile* with dual-labeled primers and an internal control
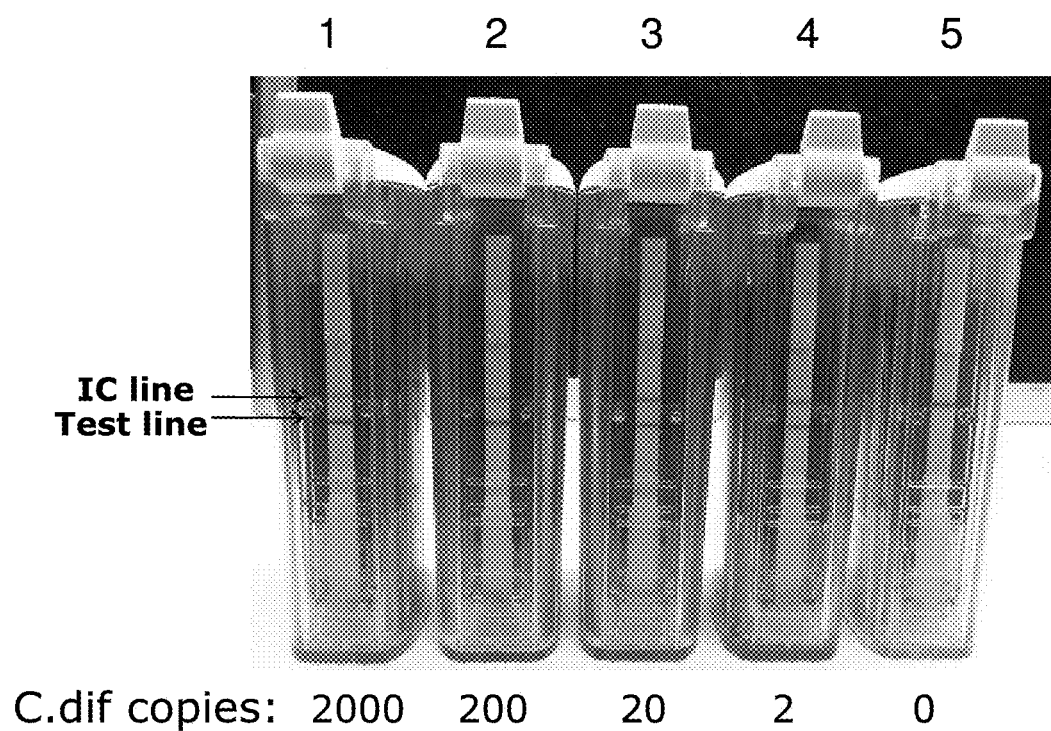

Figure 9. Splitting probes enhance the signal intensity of control line (C) in cassette detection for 2-plex HDA of MRSA.
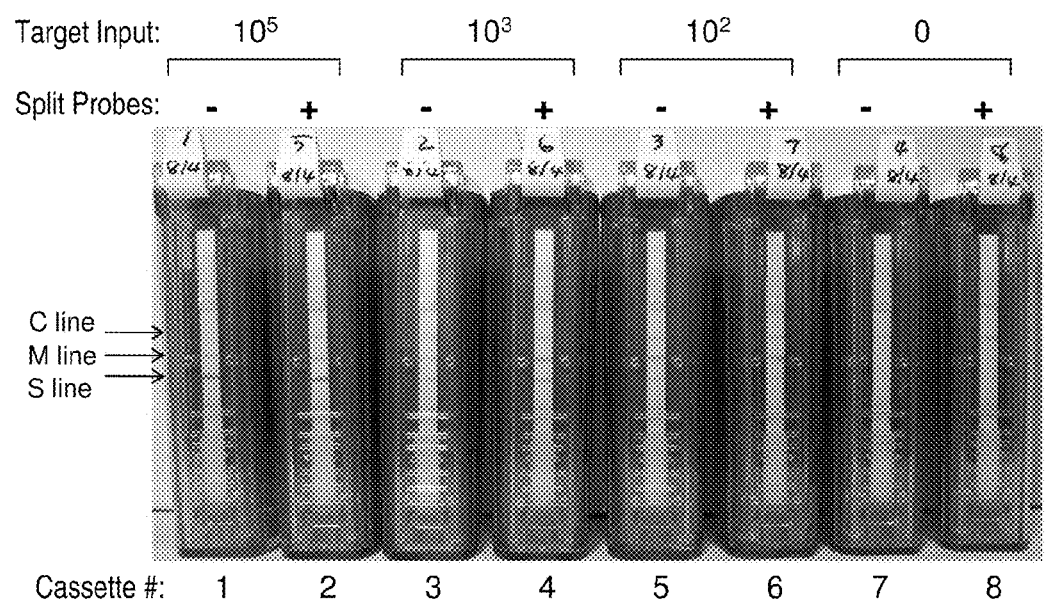

SEQUENCE LISTING

```
<160> NUMBER OF SEQ ID NOS: 22

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 5' Biotin

<400> SEQUENCE: 1
gatgttgata tgcttccagg tattcac                                           27

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tatcatttcc caacggtcta gtccaat                                           27

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 3' FITC

<400> SEQUENCE: 3
```

```
agagctaggt ctagatattg ttt                                           23

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 3' Dig

<400> SEQUENCE: 4
acgtcgtctc ttaccgatta ac                                            22

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttcaaggaga acatcgcccc gtacaa                                        26

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 5' Biotin

<400> SEQUENCE: 6
taaactggga gtagcggtgg ccgaac                                        26

<210> SEQ ID NO 7
<211> LENGTH: 114
<212> TYPE: DNA
<213> ORGANISM: Artificial Sequence
<220> FEATURE:
<223> OTHER INFORMATION: Description of Artificial Sequence: Synthetic
      HSV Internal Control Sequence, HSVIC

<400> SEQUENCE: 7
ttcaaggaga acatcgcccc gtacaaccag gacgctgcca cacctacgaa ggcgacaaag   60
agtccgcaca gtactaggcg atggtgtggt tcggccaccg ctactcccag ttta        114

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 3' FITC

<400> SEQUENCE: 8
atgtactaca aagacgt                                                  17

<210> SEQ ID NO 9
<211> LENGTH: 14
<212> TYPE: DNA
```

```
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 3' Dig

<400> SEQUENCE: 9
caaagagtcc gcac                                                         14

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 3' Dig

<400> SEQUENCE: 10
atgtactaca aagacgt                                                      17

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 5' Dig

<400> SEQUENCE: 11
tatcatttcc caacggtcta gtccaat                                           27

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gataaatatg gacgtggctt agcgtat                                           27

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tagccaagcc ttgacgaact aaagc                                             25

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gaaaaatgat tatggctcag gtactgc                                           27
```

```
<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tagacgtcat atgaaggtgt gcttaca                                              27

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 3' Bio

<400> SEQUENCE: 16
tagccaagcc ttgacgaa                                                        18

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 3' FITC

<400> SEQUENCE: 17
gtttaccatt tttccatcag cat                                                  23

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 3' Bio

<400> SEQUENCE: 18
tgattatggc tcaggtactg                                                      20

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 3' Dig

<400> SEQUENCE: 19
accctcaaac aggtgaatta tta                                                  23

<210> SEQ ID NO 20
<211> LENGTH: 20
<212> TYPE: DNA
<213> ORGANISM: Artificial Sequence
```

-continued

```
<220> FEATURE:
<223> OTHER INFORMATION: Description of Artificial Sequence: Synthetic
      probe
<220> FEATURE:
<223> OTHER INFORMATION: 3' DNP

<400> SEQUENCE: 20
accgattaac ttctcttgcc                                                    20

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 3' DNP

<400> SEQUENCE: 21
gtttaccatt tttccatcag cat                                                23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 3' DNP

<400> SEQUENCE: 22
accctcaaac aggtgaatta tta                                                23
```

DETECTION OF NUCLEIC ACID AMPLIFICATION PRODUCTS IN THE PRESENCE OF AN INTERNAL CONTROL SEQUENCE ON AN IMMUNOCHROMATOGRAPHIC STRIP

REFERENCE TO RELATED APPLICATIONS

This application claims the benefit of and priority to U.S. Provisional Patent Application No. 61/267,639, filed Dec. 8, 2009, the complete disclosure of which is incorporated by reference herein.

BACKGROUND OF THE INVENTION

Nucleic acids are commonly amplified in diagnostics, research, and forensics to preserve samples, identify pathogens and clone DNA. A variety of techniques have been developed to amplify nucleic acids. Amongst these, the polymerase chain reaction (PCR) is the most widely known. PCR, a target amplification technique (U.S. Pat. Nos. 4,683,195; 4,683,202; and 4,800,159), utilizes two oligonucleotides primers that hybridize to the 5' and 3' edges of a target sequence. A DNA polymerase extends the primers through the addition of deoxynucleoside-triphosphates (dNTPs) to create double-stranded product. The double-stranded products are separated through the use of heat and the process is repeated to generate exponential amplification of the selected target.

In addition to PCR, a variety of other methods of nucleic acid amplification have been developed. Examples of these are strand displacement amplification (SDA), which utilizes restriction enzyme nicking of a DNA strand followed by extension with an exonuclease-deficient polymerase (U.S. Pat. Nos. 5,455,166 and 5,470,723), transcription mediated amplification (TMA), which utilizes an RNA polymerase to generate an RNA copy from the target sequence, combined with a reverse transcriptase to generate DNA (U.S. Pat. Nos. 5,399,491 and 5,554,516), and ligase chain reaction (LCR), a signal amplification method (U.S. Pat. No. 5,494,810). In addition, a method has been developed that utilizes a helicase to perform in vitro strand separation for the purposes of amplification of DNA or RNA (U.S. Pat. No. 7,282,328). This method, entitled Helicase Dependent Amplification (HDA), has performance capabilities similar to PCR in an isothermal format. HDA can be performed at many different temperatures, dependent upon the polymerase and helicase selected for the assay.

The detection of amplified nucleic acids for clinical applications primarily relies upon nucleic acid hybridization to sequence-specific probes. This ensures that the product generated is the intended amplified sequence and not a spurious artifact or primer dimer. Asymmetric PCR is a method well known in the art (U.S. Pat. No. 5,066,584) and was developed to produce increased quantities of single-stranded amplicon from PCR-based amplification required for use in direct sequencing reactions and/or probe hybridization.

The hybridized probe can be visualized through a variety of methods well known in the art that include the labeling of the probe with enzymes or luminescent or fluorescent reagents. The use of probes comprised of oligonucleotide sequences bound to microparticles is also well known in the art. The detection of an amplified product with luminescent or fluorescently labeled probes requires the use of specialized equipment such as real-time thermocyclers or luminometers. Fluorescent detection of amplified nucleic acids is a rapid and sensitive method, but it significantly increases the cost of nucleic acid diagnostics. An alternative method to detect the amplified nucleic acid products is through the use of a membrane-based test strip similar to the lateral-flow immunoassays (or "dipsticks") widely used in protein detection. Lateral-flow detection is advantageous over machine-based methods in that the method can be performed with small, inexpensive and disposable devices (see, for example, U.S. Pat. Nos. 5,955,351 and 5,344,757 and US Patent Application Publication Nos. 2006/0160078 A1 and 2009/0181388 A1. Methods of lateral-flow test strip detection are well known in the art, primarily as a means to detect proteins, known as lateral-flow immunoassays. For example, non-radioactively labeled molecules such as biotin can be attached to oligonucleotide probes and captured on a solid phase support membrane for detection. Furthermore, capture may be mediated through an antibody-antigen reaction, wherein an antibody incorporated into the test strip to a hapten conjugated to the oligonucleotide is captured and visualized through dye-particles that generate a visible line. This allows for the specific detection of the amplified product on a lateral-flow test strip without any instrumentation (see, for example, US Patent Application Publication No. 2009/0181388 A1 and Goldmeyer et al., *J. Clin. Microbiol.* 46: 1534-1536 (2008)).

In nucleic acid amplification tests (NAAT), inhibitors of amplification reactions can be present in clinical samples. Inhibition of amplification can result in false negatives whereby the inability to detect the target of interest is caused by the failure of the reaction rather than the lack of target present. A false negative can result in the misdiagnosis of a disease or infection. To detect inhibition that may prevent amplification, resulting in a false negative, the use of an internal amplification control is necessary. This concept has been described for use in amplification reactions performed and monitored fluorescently in real-time thermocyclers. A variety of methods have been previously described which detail the use of internal controls for real-time amplification (see, for example, U.S. Pat. No. 6,312,929 and US Patent Application Publication Nos. 2005/0003374 A1 and 2006/0166232 A1). One internal control design, called a "competitive internal control," utilizes a single pair of primers to simultaneously amplify both a target sequence of interest and a reference "internal control" sequence that can be amplified even when the target sequence is undetectable (*J. Clin. Microbiol.* 32:1354-1356 (1994)). However, the use of an internal control in conjunction with the detection of enzymatically amplified nucleic acids on a lateral-flow strip and the methods to do so have not been previously described.

SUMMARY OF THE INVENTION

The inventors have discovered that the presence of larger amounts of a target nucleic acid in a sample can interfere with the successful co-amplification of an internal control sequence. Without wishing to be bound by theory, this is believed to result from competition for primers or other reagents in the amplification process. As a result, amplification of the internal control may be substantially reduced, complicating the interpretation of the results. If the internal control is not detected, even a successful amplification of a target nucleic acid risks being disregarded (because of the absence of the internal control) or being misinterpreted as a negative result, if the user misidentifies the single amplified product as the internal control rather than the target nucleic acid.

The invention provides methods and compositions that make it easier to confirm the success of an amplification reaction involving a target nucleic acid and a control nucleic acid. For example, the invention provides a nucleic acid assay method that includes performing a nucleic acid amplification reaction to amplify a control nucleic acid and a test nucleic acid. Amplified control nucleic acids, if present, are captured in a control capture zone. Amplified test nucleic acids, if present, are captured both in the control capture zone and in a test capture zone. In this way, successful amplification of either the control nucleic acid or the test nucleic acid provides a captured nucleic acid in the control capture zone. The captured nucleic acid can then be detected. Detection of captured nucleic acid in the control capture zone confirms that the amplification reaction was successful. In this way, the amplification reaction can be correctly interpreted, even if larger amounts of target nucleic acid reduce or eliminate the amplification of the control nucleic acid, as the amplified target nucleic acid effectively compensates for the reduced amplification of the control.

The invention also provides a composition that includes test nucleic acids immobilized at two distinct locations and control nucleic acids immobilized at one of the two locations. This composition may result, for example, from the nucleic acid assay method described above. The supplementation of control nucleic acids with test nucleic acids at one location promotes the detection of nucleic acid at that location. The additional presence of test nucleic acids at a second, distinct location (lacking control nucleic acids) permits their unambiguous identification.

In another aspect, the invention provides a composition including three nucleic acid probes useful in combination to detect target and control nucleic acids. A first nucleic acid probe includes a ligand and a sequence complementary to a target nucleic acid. A second nucleic acid probe includes the same ligand and a sequence complementary to a different, control nucleic acid. A third nucleic acid probe includes a different ligand and a sequence complementary to the target nucleic acid. Thus, two nucleic acid probes complementary to the target nucleic acid are provided, with different ligands, one of which is also present on a nucleic acid probe having a sequence complementary to a control nucleic acid. Thus, if binding moieties (such as antibodies) to the ligands are used to immobilize the nucleic acid probes at discrete locations (e.g. on discrete substrates or at discrete locations on the same substrate), one location would include nucleic acid probes complementary both to the target nucleic acid and to the control nucleic acid, whereas a second, different location would only include nucleic acid probes complementary to the target nucleic acid.

In yet another aspect, the invention provides a composition having at least two capture zones. Antibodies to a first antigen are covalently immobilized at both capture zones. Antibodies to a second, different antigen are covalently immobilized at only one of the capture zones. The composition can be used, for example, to capture at each of two capture zones a target nucleic acid labeled with one antigen, and also to capture, at one of the two zones, a control nucleic acid labeled with a different antigen.

BRIEF DESCRIPTION OF THE DRAWINGS

FIG. 1 is a schematic diagram of amplification of a target sequence in the presence of an internal control sequence and subsequent detection on a lateral-flow strip.

FIG. 2 is a schematic diagram of amplification of a target sequence using a split probe to enhance the intensity of the control line.

FIG. 3 is a schematic diagram of the use of dual capture zones to enhance the intensity of the control line.

FIG. 4 is a schematic diagram of an internal control using a labeled primer.

FIG. 5 is a photograph of the detection of an amplified target sequence and an amplified internal control sequence.

FIG. 6 provides photographs of the detection of amplified target and internal control sequences without (Panel A) or with (Panel B) the use of a split probe.

FIG. 7 provides photographs of the detection of amplified target and internal control sequences with varying amounts of target nucleic acid and varying amounts of nucleic acid probes, as well as graphical depictions of the increase in observed signal with increasing cycle number.

FIG. 8 is a photograph of the detection of amplified target and internal control sequences using dual-labeled primers.

FIG. 9 is a photograph of the detection of amplified MRSA using split probes.

DETAILED DESCRIPTION OF THE INVENTION

The use of an internal control is essential in clinical diagnostics because clinical samples often contain inhibitory substances. Implementation of an internal control can reduce false negative results due to specimen inhibition, amplification failure, or device failure. The successful, reliable implementation of internal controls in amplification-based assays is complicated by the unknown concentrations of target nucleic acid in a sample, concentrations that may vary by several orders of magnitude.

These complications can be seen, for example, in detection of amplified target and internal control (IC) sequences on a lateral-flow test strip. The same pair of 5'- and 3'-primers could be used in the assay to amplify the target sequence as well as an IC sequence, which are subsequently hybridized by the corresponding labeled probes (see FIG. 1). Different pairs of primers may also be used to amplify the target sequence and the control sequence. Duplexes consisting of the target-amplicon and its labeled probe (e.g. FITC) are captured by antibodies (e.g. anti-FITC) previously sprayed onto the membrane as a test-line while hybrids containing the IC-amplicon and its probe (e.g. DIG) are captured by (anti-DIG) antibodies previously sprayed onto the membrane as the control-line. A nucleic acid template containing the IC sequence is always present in the assay and its concentration should be carefully calibrated. If the concentration present is too low relative to the expected target, consistent amplification is difficult to achieve. If the concentration is too high relative to the expected target then the sensitivity of the assay can be compromised. If the target sequence is present in a sample, both the target sequence and IC sequence should be amplified and detected, resulting in a positive test line and control line (FIG. 1, Positive). If the target sequence is absent in a sample, only the internal control (IC) sequence is amplified and detected on the control line (FIG. 1, Negative). If neither the target nor the IC sequence is detected, the test is invalid because the lack of a visible result could have been caused by amplification reagent failure, device failure, or specimen inhibition (FIG. 1, Invalid). In some cases, the target sequence may be present in a large excess over the IC sequence. Due to the competitive nature of the amplification reactions, the amplification product of the IC sequence might be very limited and difficult to detect, especially in the lateral-flow format due to a higher threshold for the detection of products as compared to a real-time fluorescent method (see FIG. 1, High Positive).

Traditional IVD laboratories are trained to interpret the test results as invalid if the control line is absent on a lateral-flow strip device regardless of the presence of the test line. Thus, larger quantities of target nucleic acid may result in the test results being discarded as invalid.

The present invention solves this problem, accommodating this traditional interpretation format and ensuring that the control line will be positive even in the presence of large amounts of target sequence. One solution provided by the present invention is to divide the target detection probe into two groups: one group is labeled with the same moiety utilized for the target probe and the other group is labeled with the same moiety utilized for the control line. In the example shown in FIG. 2, one group of target detection probes is labeled with FITC for visualization at the test line; the other group of target detection probes is DIG-labeled for visualization at the control line (FIG. 2). By using this split probe design, the control line is always visible even in the presence of high concentrations of the target, while its ability to monitor inhibition and amplification/or device failure in tests with negative samples remains unchanged.

Design of Internal Control Probes for Lateral Flow Strip Format

As depicted in FIG. 1, an amplification reaction is performed to amplify and detect a specific target sequence of a nucleic acid molecule. In the amplification reaction, two primers are present in this particular example. In one example, the reverse primer contains a biotin label, but the label can be selected from a variety of different haptens or conjugates known in the art. The amplification reaction is carried out asymmetrically by using the labeled primer in excess of the unlabeled primer such that single-stranded amplicon with a desired label (such as biotin) is generated. An oligonucleotide probe is present in the reaction that hybridizes specifically to the labeled single-stranded amplicon. In this example, the oligonucleotide probe contains FITC conjugated to one end which will hybridize to the amplicon with, for example, a biotin label to form a dual-labeled hybrid. An internal control (IC) template is also present in the amplification reaction. The IC can be spiked into the clinical sample prior to any preparation steps or can be added with the amplification reagents. This IC sequence can be amplified by the same forward and reverse primers as the intended target; however the internal sequence is unrelated, usually a random sequence that is not found in nature. Nevertheless, the IC sequence can also be amplified by a different pair of primers. A second probe, specific for the IC sequence is present in the reaction. This probe is conjugated to a different moiety than the target probe, in this example the moiety is DIG. The FITC-labeled target probes hybridizes to the biotinylated complementary target DNA strand during the amplification reaction, generating FITC/Biotin dual labeled nucleic acid molecules when a target sequence in present in the assay. Likewise, the DIG-labeled Internal Control (IC) probes hybridize to the biotinylated IC template during the amplification reaction, generating DIG/Biotin dual-labeled nucleic acid molecules when the amplification reaction works and is not inhibited. After the amplification reaction, a portion or all of the reaction is applied to a test strip that contains a minimum of two lines, a test line striped with an antibody to moiety 1 (FITC) to capture the FITC/Biotin dual-labeled target of interest and a control line striped with the antibody to moiety 2 (DIG) to capture the DIG/Biotin dual-labeled internal control (IC) (FIG. 1). The captured biotinylated nucleic acid molecules are visualized by the binding of streptavidin-colored particle conjugates to the biotin label. If a sample contains the target sequence, both the target sequence and the IC sequence are amplified, resulting in a positive test line and a positive control line (FIG. 1, Positive). If the target sequence is absent in a sample, only the internal control (IC) sequence should be amplified and detected on the control line (FIG. 1, Negative). If no lines are visualized then either the reaction or the device has failed and the assay must be repeated (FIG. 1, Invalid). In some cases, the target sequence may be present in a large excess over the IC sequence. Due to the competitive nature of the amplification, the amplification product of the IC sequence might be very limited and difficult to be detected, especially in the lateral-flow format because the control line is usually striped at the position that is farther away from the flow direction (see FIG. 1, High Positive).

Split-Probe Design

In the presence of overwhelming amounts of target nucleic acid, the amount of internal control amplicon generated may be insufficient to be detected on the control line of a test strip. One way to enhance the signal at the control line is to split the detection probe for the target sequence into two groups, one group for the visualization of said target at the corresponding test line and the other for the visualization of the control line. Even when a limited internal control amplicon is made in the presence of overwhelming amounts of target nucleic acid, part of the target amplicon tagged for the control line will be detected at the control line in order to generate a visible line (FIG. 2).

In the example illustrated in FIG. 2, the methodology employed is the same as depicted in FIG. 1, with the exception that two groups of target detection probes are used. One group (the target detection probe for the test line) is labeled with one label such as FITC, which will be captured at the test line via anti-FITC antibodies. The second group (the target detection probe for the control line) is labeled with a different label, for example DIG, which will be captured at the control line via anti-DIG antibodies. If a sample contains the target sequence, both the target sequence and the IC sequence are amplified, resulting in a positive test line and a positive control line (FIG. 2, Positive). If the target sequence is absent in a sample, only the internal control (IC) sequence will be amplified and detected on the control-line (FIG. 1, Negative). If no lines are visualized then either the reaction or the device has failed and the assay must be repeated (FIG. 1, Invalid). If the target sequence is present in large excess over the IC sequence, limited amplification product with the DIG-probe and biotinylated amplicon will be generated. However, in the split probe design, the excess target amplicons consist of two groups: one group contains the FITC-probe hybridized to biotinylated amplicon which will be captured by the anti-FITC antibodies at the test line while the second group contains the DIG-probe hybridized to biotinylated target-amplicon which will be captured by the anti-DIG antibodies at the control line, resulting in an enhanced control line even in high positive sample (FIG. 2, High Positive).

The ratio of the target detection probe for the test line to the target detection probe for the control line may be, for example, 10:1, or 4:1, or 2:1, or 1:1, or 1:2, or 1:4 (see Example 3). The optimal ratio of the target detection probe for the test line versus the target detection probe for the control line can be determined experimentally such that the splitting of the detection probe has a minimal impact on the detection sensitivity of the assay while enhancing the control line visualization to a detectable level.

Dual Capture Zone Design

Another way to enhance the signal at the control line is to trap a portion of the target amplicon(s) at the control line by dividing the capture reagents for said target amplicon into at least two zones: one is positioned at the corresponding test line for said target and the other group is positioned at the control line (FIG. 3).

In the event such that the target sequence is present in a large excess over the IC sequence, limited amplification products with DIG-probe and biotinylated amplicon will be generated, resulting in a very weak signal at the control line (FIG. 3, Regular strip). However, in the dual capture zone design, the capture reagents (for example anti-FITC antibodies) for the target amplicon are placed in both detection zones, the test line for the target amplicons and the control line for the IC amplicon. The excess target amplicons with the FITC label can overflow the first capture zone (anti-FITC Ab at the test line) and be captured at the second capture zone (anti-FITC Ab at the control line), resulting in an enhanced control line even when a high positive sample occurs (FIG. 3, Strip with dual capture zones).

The optimal ratio of the target detection capture reagents for the test line versus the target detection capture reagents for the control line can be determined experimentally such that the splitting of the capture reagents has minimal impact on the detection sensitivity of the assay while enhancing the control line visualization to a detectable level.

Internal Control Using a Labeled Primer

In certain amplification reactions, the addition of an internal control probe may cause inhibition of the amplification reaction. In those cases, one can utilize a labeled primer (for example the 5'-primer can be labeled with DIG), rather than a sequence-specific probe in the reaction. In this example, as the internal control sequence and the target of interest share the same forward and reverse primers for amplification, both the internal control and the target amplicon will be detected on the control line. When the target nucleic acid is present, the amplicon generated will be detected via the probe labeled with FITC and visualized on the test line (FIG. 4, Positive). In the absence of target nucleic acid, only the internal control will be amplified and detected via dual-labeled primers (DIG labeled 5'-primer and biotinylated 3'-primer) on the control line (FIG. 4, Negative). In the event that the amplification reaction does not work or the device malfunctions, there will be no line detected, thus generating an invalid result (FIG. 4, Invalid). In addition, both the internal control and the target amplicon will be detected on the control line due to the DIG labeled 5'-primer and biotinylated 3'-primer. If the target sequence is present in large excess over the IC sequence, overflow target amplicons with DIG labeled 5'-primer and biotinylated 3'-primer will be captured by anti-DIG antibodies at the control line, resulting in an enhanced control line even in the event of a high positive sample (FIG. 4, High Positive).

All references cited herein are incorporated by reference.

EXAMPLES

Example 1

Amplification of a Target of Interest in the Presence of an Internal Control and Subsequent Detection on Lateral Flow Strip In this example, the target of interest is the toxin A (tcdA) gene of *Clostridium difficile* (CD), one of the indicators of *C. difficile*-associated diarrhea (CDAD). The internal control (IC) template contains a randomly selected DNA fragment flanked by the same primer pair used for amplification of the target tcdA sequence cloned into a plasmid. An asymmetric tHDA reaction was carried out using a pair of primers, Bio-CDTAF1 (SEQ ID NO:1) and CDTAR1 (SEQ ID NO:2), which target a conserved region of the toxin A (tcdA) gene of *C. difficile*, in the presence of an IC template, a target probe, and an IC probe. Other amplification methods (i.e. PCR) can also be used to amplify the target and IC sequence. To perform asymmetric tHDA, the excess primer, BioCDTAF1, was labeled with biotin at its 5'-end. The target probe, CDTAP3FI (SEQ ID NO:3), was labeled with fluorescein (FITC) at its 3'-end and is complementary to the single-stranded target amplicon of tcdA gene with biotin label. The IC probe, ICDig1 (SEQ ID NO:4), is labeled with digoxigenin (Dig) at its 3'-end and is complementary to the single-stranded, biotin-labeled IC amplicon.

10-fold serial dilutions of purified CD genomic DNA (ATCC 9689D-5) from 2000 copies down to 2 copies were each spiked into 2 µl of purified CDAD negative stool DNA and used as a template. Each CDAD negative stool DNA was purified from 200 mg of CDAD negative stool samples (Beth Israel Deaconess Medical Center, Boston, Mass.) using a QIAamp DNA Stool Mini Kit (QIAGEN Inc, Valencia, Calif.) and eluted into 200 µl elution buffer. The tube containing the amplicons was then detected by the BESt™ cassette (BioHelix Corp., Beverly, Mass.). The lateral-flow DNA test strip embedded in the BESt™ cassette was pre-striped with an anti-FITC antibody, which serves as the test line, and an anti-DIG antibody, which serves as the IC line in the lateral-flow assay. A test line is visible only when the target probe hybridizes with the amplified tcdA gene product. An IC line is visible only when the IC probe hybridizes with the amplified IC product. No line is visible when the tHDA reaction or the flow of the device fails.

The tHDA reaction with a total volume of 50 µl was set up using an IsoAmp II Kit (BioHelix Corp, Beverly, Mass.). The reaction was assembled in one sterile microtube by combining:

5 µl 10× Annealing Buffer II
2 µl 10-fold serial dilutions of CD genomic DNA (1000 to 1 copy/µl)
2 µl purified CDAD negative stool DNA
5 µl IC Plasmid DNA ($10^4$ copies/µl)
2 µl 5 µM BioCDTAF1 primer
1 µl 5 µM CDTAR1 primer
0.4 µl 5 µM CDTAP3FI probe
0.4 µl 5 µM ICDig1 probe
2 µl 100 mM $MgSO_4$
4 µl 500 mM NaCl
3.5 µl IsoAmp dNTP Solution
3.5 µl IsoAmp Enzyme Mix
19.2 µl $dH_2O$
Total volume: 50 µl For the negative control reaction, replace CD genomic DNA with 2 µl $dH_2O$.

The tHDA reaction was carried out at 65° C. for 90 min. After completion of the tHDA reaction, the reaction tube was transferred to an amplicon-containing, disposable cartridge with a lateral-flow strip (Type II BESt™ Cassette, BioHelix Corp., Beverly, Mass.). Closing the cartridge lid triggers the release of the reactants from the tube at the bottom of the analysis cassette. The amplified product was detected by lateral flow on a strip embedded in the cartridge.

Results are illustrated in FIG. 5. A positive test line was seen from the lateral-flow cassette loaded with amplified tHDA product from an input CD genomic DNA of 2000 copies to 2 copies but not from the negative control reaction. An IC line was seen from all tHDA reactions include the negative control reaction, although the intensity of the IC line dropped from the tHDA reaction of 2000-copy input CD genomic DNA due to overwhelming amounts of target molecules. This demonstrates that the IC probe can be used for specific IC detection in the lateral-flow assay. The IC can monitor the amplification process and serve as an indicator whether an inhibitor is present in the tHDA reaction. The results also indicate that tHDA can specifically amplify the CD tcdA gene in a background of CDAD negative stool DNA. The analytical sensitivity of lateral-flow tHDA assay in the presence of an IC reaches as low as 2 copies of CD genomic DNA.

Example 2

Use of Split Probe Design to Amplify and Detect a Target Sequence in the Presence of an Internal Control Sequence In this example, a method is disclosed to enhance the control line by using a split probe design in which the detection probe for the target sequence is split into two groups, one group for the visualization of the target amplicon at the corresponding test line and the other for the visualization of the target amplicon at the control line. In this example, the target of interest is a specific sequence in the human herpes simplex virus type 2 (HSV-2; Genbank accession No. AB442016 REGION: 424-523, 100 bp). A specific forward primer, HSVF (SEQ ID NO: 5), and biotin-labeled reverse primer, BioHSVR (SEQ ID NO: 6), were used to amplify the 100 bp HSV-2 fragment. The internal control for the HSV assay was constructed by cloning a random sequence flanked by the HSVF and BioHSVR primer sequences (HSVIC, SEQ ID NO: 7) into a pCR-Blunt II-TOPO plasmid (Invitrogen, Carlsbad, Calif.) and named as HSVIC-TOPO. The HSV template containing the target sequence (HSV-2 G Strain Quantitated Viral DNA, named as HSV2) was purchased from Advanced Biotechnologies Inc. (Columbia, Md.). The specific detection probe for HSV, HSV-FITC probe (SEQ ID NO: 8), can be captured by the anti-FITC antibody present on the lateral flow strip to form the test line (T). The specific detection probe for HSVIC was named HSVIC-DIG probe SEQ ID NO: 9), which could be captured by the anti-DIG antibody to form the control line (C). In order to form a visible C line when there is an excess amount of target HSV amplicon, but not enough internal control amplicon, another detection probe for the HSV target was added into the reaction, HSV-DIG probe (SEQ ID NO: 10). This additional HSV-DIG probe is referred to as the split probe from the HSV-FITC probe. All the primers and probes were purchased from IDT (Coralville, Iowa).

The asymmetric tHDA reaction was performed first by combining the following components to produce a reaction master mix with a final volume of 45 µl/reaction (the number of reaction master mix is the number of tested samples +2. For example, if 5 samples were to be tested, 7 reactions of master mix were prepared):

Reaction master mix 1 (w/o split probe):
5 µl 10× Annealing buffer II
0.3 µl 5.0 µM HSVF primer (SEQ ID NO: 5)
0.9 µl 5.0 µM BioHSVR primer (SEQ ID NO: 6)
0.2 µl 5.0 µM HSV-FITC probe (SEQ ID NO: 8)
0.3 µl 5.0 µM HSVIC-DIG probe (SEQ ID NO: 9)
1 µl 2000 copies/µl HSVIC-TOPO plasmid (SEQ ID NO: 7)
2.1 µl 100 mM MgSO₄
2.0 µl 500 mM NaCl
2.0 µl 10 mM dNTP
1.5 µl 100 mM dATP
3.5 µl IsoAmp Enzyme Mix (IsoAmpII Universal tHDA Kit, BioHelix, Beverly, Mass.)

1.0 µl AvaII restriction endonuclease (New England Biolabs, Ipswich, Mass.)
add dH₂O to total 454
Reaction master mix 2 (w/ split probe):
5 µl 10× Annealing buffer II
0.3 µl 5.0 µM HSVF primer (SEQ ID NO: 5)
0.9 µl 5.0 µM BioHSVR primer (SEQ ID NO: 6)
0.2 µl 5.0 µM HSV-FITC probe (SEQ ID NO: 8)
0.2 µl 5.0 µM HSV-DIG probe (SEQ ID NO: 10)
0.3 µl 5.0 µM HSVIC-DIG probe (SEQ ID NO: 9)
1 µl 2000 copies/µl HSVIC-TOPO plasmid (SEQ ID NO: 7)
2.1 µl 100 mM MgSO₄
2.0 µl 500 mM NaCl
2.0 µl 10 mM dNTP
1.5 µl 100 mM dATP
3.5 µl IsoAmp Enzyme Mix (IsoAmpII Universal tHDA Kit, BioHelix, Beverly, Mass.)
1.0 µl AvaII restriction endonuclease (New England Biolabs, Ipswich, Mass.)
add dH₂O to total 454

To prepare an HDA reaction, 5 µl of varying amounts of target (HSV2) was added to individual PCR reaction tubes. In order to compare the effects of the split probe, two identical sets of reactions were prepared. For each set, the following target inputs were utilized: 50,000 copies/reaction (high copy number of target), 100 copies/reaction (near the LoD of the assay), and dH₂O (NTC). 45 µl of reaction master mix 1 was added to one set of tubes, 45 µl of reaction master mix 2 was added to the other set of tubes. The reactions were mixed by pipetting up and down several times and then covered with mineral oil. The reaction mixture was immediately incubated in 65° C. incubator (digital heat block, digital water bath or thermocycler).

After 1 hour, specific amplification was detected by type II BESt™ cassette (BioHelix Corp., Beverly, Mass.) which contains two detection lines: a Test line with anti-FITC antibodies labeled as "T" and a Control line with anti-DIG antibodies labeled as "C" (FIG. 6). The results showed that without the split probe (HSV-DIG probe), the control line (C) was hardly visible even in the samples containing close to the LoD of target molecules (FIG. 6, Panel A, 100 copies/reaction). On the other hand, when the split probe (HSV-DIG probe) was present in the reaction, the C line was clearly present even in the presence of high copy number target input (FIG. 6, Panel B, 50,000 copies/reaction). The results in FIG. 6 illustrate that the intensity of the control line can be enhanced by splitting the target detection probes.

Example 3

Determine the Optimum Ratio of the Split Probes

The optimal ratio of the target detection probe for the test line versus the target detection probe for the control line can be determined experimentally such that the splitting of the detection probe has minimal impact on the detection sensitivity of the assay while enhancing the control line to a detectable level.

In this example, a method is disclosed to optimize the detection probe concentrations. Generally, the optimization was performed with at least two different concentrations of the target input. One optimization was performed with a high copy number of target to address the following question: What is the minimal amount of the target detection probe required for the control line when there is almost no internal control DNA being amplified? In this situation, the presence of the control line solely depends on the amount of the target detection probe utilized for the control line. Another optimization was performed with low copy number (close to LoD) of target to address the following question: What is the maximal amount of the target detection probe for the control line in a situation where the input of the target is near the Limit of Detection (LoD)? In this situation, it is desirable that the addition of the target detection probe for the control line will not weaken the visibility of the target detection, resulting in a loss of sensitivity in the assay.

The same primers, probes and enzymes for the HDA amplification system were utilized as detailed in Example 2. To answer the first question, HDA reaction A was performed by combining the following components to produce a reaction master mix with a final volume of 45 µl/reaction (the number of reaction master mix required is the number of tested samples +2. In this case, a reaction mix of 12× was prepared:

5 µl 10× Annealing buffer II
0.3 µl 5.0 µM HSVF primer (SEQ ID NO: 5)
0.9 µl 5.0 µM BioHSVR primer (SEQ ID NO: 6)
0.2 µl 5.0 µM HSV-FITC probe (SEQ ID NO: 8)
0.3 µl 5.0 µM HSVIC-DIG probe (SEQ ID NO: 9)
1 µl 2000 copies/µl HSVIC-TOPO plasmid (SEQ ID NO: 7)
0.5 µl 100,000 copies/µl HSV2 (example of high copy number of target)
2.1 µl 100 mM $MgSO_4$
2.0 µl 500 mM NaCl
2.0 µl 10 mM dNTP
1.5 µl 100 mM dATP
0.5 µl EvaGreen (20×, Biotium, Hayward, Calif.)
1 µl ROX dye (50×, Invitrogen, Carlsbad, Calif.)
3.5 µl IsoAmp Enzyme Mix (IsoAmpII Universal tHDA Kit, BioHelix, Beverly, Mass.)
1.0 µl AvaII restriction endonuclease (New England Biolabs, Ipswich, Mass.)
add $dH_2O$ to total 454

To prepare the HDA reactions, 5 µl of varying amounts of the target detection probe for the control line (HSV-DIG probe; SEQ ID NO: 10) were added to individual amplification reaction tubes (e.g.: 5 nM/assay vs. 10 nM/assay). Each concentration was tested four times. Two reactions were set up as negative controls by adding 5 µl of $dH_2O$ instead of target. 45 µl of reaction master mix were added to individual PCR reaction tubes. The reactions were mixed by pipetting up and down several times and then covered with mineral oil. The reaction mixture was immediately incubated in an ABI7300 real-time PCR machine with the well inspector setting: reporter dye: SYBR; quencher: none; passive reference dye: ROX. ABI7300 real-time PCR instrument is used for the detection of the HDA amplification products in real-time such that minor differences among different assay conditions can be compared and analyzed. To perform isothermal reactions in an ABI7300 real-time PCR instrument, which requires a minimum of 1 degree of temperature variation between different cycles, the following program was used:

Stage 1: (30×)
Step 1: 64.5° C. for 0:05
Step 2: 63.5° C. for 1:55 (Data collection and real-time analysis enabled)

After 1 hour, the tubes were removed from the ABI instrument and specific amplification was detected by the type II BESt™ cassette. Results are shown in FIG. 7. Panel A showed that with different amounts of HSV-DIG probe, the real-time signals were identical, which suggested that the amplification efficiencies were similar. However, 10 nM HSV-DIG probe (the probe ratio for test line vs. control line=2:1) could generate a much clearer signal on the control line as compared to the 5 nM HSVP-DIG probe (probe ratio for test line vs. control line=4:1).

To answer the second question, HDA reaction B was performed by preparing a reaction master mix with a final volume of 45 µl/reaction. The components were identical to reaction A, except that 0.5 µl of 100,000 copies/µl HSV2 was replaced with 0.5 µl of 1,000 copies/µl HSV2 to evaluate the effects of a lower quantity of target in the reaction.

To prepare the HDA reactions, 5 µl of varying amounts of the target detection probe for the control line (HSV-DIG probe) was added to individual PCR reaction tubes (e.g. 10 nM/assay vs. 20 nM/assay. Each concentration was tested four times. Two reactions were set up as negative controls by adding 5 µl of $dH_2O$ instead of target input. 45 µl of reaction master mix were then added to each individual amplification reaction tube. The reactions were mixed by pipetting up and down several times and then covered with mineral oil. The reaction mixture was immediately incubated in an ABI7300 real-time PCR machine with the same program as used in reaction setup A.

After 1 hour, the samples were removed from the ABI machine and specific amplification was detected by the Type II BESt™ cassette. Results are depicted in FIG. 7. Panel B showed that with different amounts of HSV-DIG probe, the real-time signals were identical, which indicated that the amplification efficiencies were similar. However, 20 nM HSVP-DIG probe (probe ratio for test line vs. control line=1: 1) generated a much clearer signal on the control line as compared with 10 nM HSVP-DIG probe (probe ratio for test line vs. control line=2:1) while the intensity of the T line at low target input remains the same. Therefore, in this example, 20 nM HSV-DIG probe (1:1 ratio) was determined to be the optimum concentration for this particular assay.

Example 4

Use of Dual-Labeled Primers for Internal Control Detection in the Lateral Flow Detection of the *C. difficile* tHDA Product In this example, asymmetric tHDA was carried out using a pair of dual-labeled primers, BioCDTAF1 (SEQ ID NO:1) and DigCDTAR1 (SEQ ID NO:11), which target a conserved region of the toxin A (tcdA) gene of *C. difficile* (CD), one of the indicators of *C. difficile*-associated diarrhea (CDAD), in the presence of an internal control (IC) plasmid and a specific target probe. The IC plasmid contains a randomly selected DNA fragment flanked by the same tcdA primer pair used for the asymmetric tHDA reaction. The excess primer, BioCD-TAF1, was labeled with biotin on its 5' end. The limiting primer, DigCDTAR1, was labeled with digoxigenin (Dig) on its 5'-end. The target probe, CDTAP1FI (SEQ ID NO:3), with its sequence complementary to the DNA strand generated from the excess primer in the tcdA gene amplification, was labeled with fluorescein (FITC) on its 3' end. 10-fold serial dilutions of purified CD genomic DNA (ATCC 9689D-5) starting from 2000 copies down to 2 copies were each spiked into 2 µl of purified CDAD negative stool DNA and used as template. Each CDAD negative stool DNA was purified from 200 mg of CDAD negative stool sample (Beth Israel Deaconess Medical Center, Boston, Mass.) using a QIAamp DNA Stool Mini Kit (QIAGEN Inc, Valencia, Calif.) and eluted into 200 µl elution buffer. The tHDA product was then directly applied for detection on a test strip in the vertical-flow cassette (Ustar Biotechnologies Ltd, Hanzhou, P. R. China). The DNA test strip embedded in the cassette was pre-striped with an anti-FITC antibody, which serves as the test line, and an anti-Dig antibody, which serves as the IC line in the lateral-flow assay. A test line is displayed only when the target probe hybridizes with the amplified tcdA gene product. An IC line is visualized as long as an amplified product was generated from the tHDA reaction. The amplified product could be a CD tcdA gene product, or an IC product, or a non-specific product like primer-dimer. No line is displayed when no amplification occurs in the tHDA reaction due to inhibition or reagent failure or when the lateral-flow device fails.

The tHDA reaction with a total volume of 50 µl was set up using an IsoAmp II Kit (BioHelix Corp, Beverly, Mass.). The reaction was assembled in one sterile microtube by combining:

5 µl 10× Annealing Buffer II
2 µl 10-fold serial dilutions of CD genomic DNA (1000 to 1 copy/µl)
2 µl purified CDAD negative stool DNA
5 µl IC Plasmid DNA ($10^3$ copies/µl)
2 µl 5 µM BioCDTAF1 primer (SEQ ID NO:1)
1 µl 5 µM DigCDTAR1 primer (SEQ ID NO:11)
0.5 µl 5 µM CDTAP1FI probe (SEQ ID NO:3)
2 µl 100 mM $MgSO_4$
4 µl 500 mM NaCl
3.5 µl IsoAmp dNTP Solution
3.5 µl IsoAmp Enzyme Mix
19.5 µl $dH_2O$
Total volume: 50 µl For the negative control reactions, replace CD genomic DNA with 2 µl $dH_2O$.

The tHDA reaction was carried out at 65° C. for 90 min. After completion of the tHDA reaction, the reaction tube was transferred to an amplicon-containing, disposable cartridge with a lateral-flow strip (Type II BESt™ Cassette, BioHelix Corp., Beverly, Mass.). Closing the cartridge lid triggers the release of the reactants from the tube at the bottom of the analysis cassette. The amplified product was detected by lateral flow on a strip embedded in the cartridge.

Results are illustrated in FIG. 8. A positive test line was visualized on the lateral-flow strip in the cassette containing the amplified tHDA product from an input CD genomic DNA of 2000 copies to 2 copies but not from the negative control reaction. An IC line with equal intensity was seen from all tHDA reactions include the negative control reaction. This demonstrates that the dual-labeled primers can be used for IC detection in the lateral-flow assay. The results also indicate that tHDA can specifically amplify the CD tcdA gene in a background of CDAD negative stool DNA. The analytical sensitivity of lateral-flow tHDA assay in the presence of an IC reaches as low as 2 copies of CD genomic DNA.

Example 5

Use of Multiple Splitting Probes for the Detection of Multiplex Amplification Product on the Lateral Flow Strip In this example, 2-plex asymmetric HDA was carried out for simultaneous amplification of nuc gene and mecA gene of MRSA using a pair of nuc gene specific primers, NUCF14 (SEQ ID NO:12) and NUCR3 (SEQ ID NO:13), and a pair of mecA gene specific primers, SAMF2 (SEQ ID NO:14) and SAMR5 (SEQ ID NO:15), in the presence of an internal control (IC) plasmid, two nuc gene target probes, two mecA gene target probes and an IC probe with or without the two splitting probes. The IC plasmid contains a randomly selected DNA fragment flanked by the same nuc primer pair used in the 2-plex HDA. Instead of placing a detection label (such as biotin) in the primer and a capturing label (such as FITC) in the probe as described in previous examples, in this example we describe an alternative method of placing both labels in two detection probes. The nuc gene target probes, NUCP1Bio (SEQ ID NO:16) and NUCP1FI (SEQ ID NO:17), with their sequence complementary to the DNA strand generated from the excess primer NUCF14 in the nuc gene amplification, was labeled with either biotin (Bio) for NUCP1Bio or fluorescein (FITC) for NUCP1FI at its 3' end. The mecA gene target probes, MECAP3Bio (SEQ ID NO:18) and MECAP2Dig (SEQ ID NO:19), with their sequence complementary to the DNA strand generated from the excess primer SAMR5 in the mecA gene amplification, was labeled with either biotin (Bio) for MECAP3Bio or digoxigenin (Dig) for MECAP2Dig at its 3' end. The IC probe, ICDNP4 (SEQ ID NO:20), with its sequence complementary to the IC DNA fragment, was labeled with 2,4-dinitrophenol (DNP) at its 3' end. In addition, the nuc gene target probe NUCP1FI (SEQ ID NO:17) was split into two groups: the original NUCP1FI probe for visualization nuc amplicon at the test line (S line) via anti-FITC antibodies and the additional NUCP1DNP probe (SEQ ID NO:21), which has identical sequence to nuc gene target probe NUCP1FI but a different DNP label at its 3' end, for visualization of nuc amplicon at the control line via anti-DNP antibodies. Similar to the nuc gene target probe, the mecA gene target probe was also split into two groups. The additional splitting probe MECAP2DNP (SEQ ID NO:22), with its sequence identical to mecA gene target probe MECAP2Dig, was labeled with DNP at its 3' end for visualization of the mecA amplicon at the control line via anti-DNP antibodies.

Purified MRSA genomic DNA (ATCC 33591) of $10^5$ copies, $10^3$ copies, $10^2$ copies and 0 copy per test was used as template in the 2-plex HDA. The 2-plex HDA product was then directly applied for lateral-flow detection using a Type 3 BESt™ cassette (BioHelix Corp, Beverly, Mass.). The DNA test strip embedded in the cassette was coated, from bottom to top, with an anti-FITC antibody, which serves as the Staph (S) line, an anti-Dig antibody, which serves as the MecA (M) line, and an anti-DNP antibody, which serves as the Control (C) line in the lateral-flow assay. The S line and (or) M line are (is) displayed only when the target probes hybridize with the amplified nuc gene and (or) mecA gene products. In the absence of the splitting probes, a C line is displayed only when the IC probe hybridizes with the amplified IC product. In the presence of the splitting probes, a C line is displayed whenever an IC product, or/and a nuc gene product, or/and a mecA gene product is (are) generated. No line is displayed when the 2-plex HDA reaction or the lateral-flow device fails.

The 2-plex HDA reaction with a total volume of 50 µl was set up using an IsoAmp II Kit (BioHelix Corp, Beverly, Mass.). A Heat Mix with or without the splitting probes was assembled in one sterile microtube by combining the following to a volume of 25 µl: Heat Mix without the splitting probes:

2.5 µl 10× Annealing Buffer II
5 µl MRSA genomic DNA ($2 \times 10^4$, or 200, or 20, or 0 copy/µl)
5 µl IC Plasmid DNA ($10^4$ copies/µl)
0.72 µl 5 µM NUCF14 primer
0.4 µl 5 µM NUCR3 primer
0.57 µl 5 µM SAMF2 primer
1.08 µl 5 µM SAMR5 primer
1.75 µl 100 mM $MgSO_4$
7.98 µl $dH_2O$ Heat Mix with the splitting probes:
2.5 µl 10× Annealing Buffer II
5 µl MRSA genomic DNA ($2\times10^4$, or 200, or 20, or 0 copy/µl)
5 µl IC Plasmid DNA ($10^4$ copies/µl)
0.72 µl 5 µM NUCF14 primer
0.4 µl 5 µM NUCR3 primer
0.57 µl 5 µM SAMF2 primer
1.08 µl 5 µM SAMR5 primer
1.75 µl 100 mM $MgSO_4$
0.2 µl 5 µM NUCP1DNP probe
0.2 µl 5 µM MECAP2DNP probe
7.58 µl $dH_2O$ The Heat Mix was then incubated in a heat block at 95° C. for 3 minutes and put on ice. A Reaction Mix was then assembled in one sterile microtube by combining the following to a volume of 25 µl:
2.5 µl 10× Annealing Buffer II
0.2 µl 5 µM NUCP1Bio probe
0.2 µl 5 µM NUCP1FI probe
0.2 µl 5 µM MECAP3Bio probe
0.2 µl 5 µM MECAP2Dig probe
0.2 µl 5 µM IC4DNP probe
4 µl 500 mM NaCl
3.5 µl IsoAmp dNTP Solution
3.5 µl IsoAmp Enzyme Mix
10.5 µl $dH_2O$ The HDA reaction was assembled in one 0.2-ml thin wall PCR tube by mixing 25 µl Heat Mix with 25 µl Reaction Mix and incubated in a heat block at 65° C. for 60 minutes. After completion of the HDA reaction, the reaction tube was transferred to an amplicon-containment, disposable cartridge. Closing the cartridge lid triggers the releasing of the amplified DNA from the tube by a razor blade lodged at the bottom of the DNA analysis cassette. The amplified product was detected by a DNA test strip embedded in the cartridge in less than 5 minutes.

Results are illustrated in FIG. 9. In the absence of the splitting probes, intensity of the C line dropped along with the increased MRSA genomic DNA copy input from 0 to $10^2$ and $10^3$ copies/test (FIG. 9, see "−" cassettes #7, 5, and 3) and the C line was invisible at target MRSA DNA input of $10^5$ copies/test (FIG. 9, cassette #1). In contrast, the C line was visible from all target DNA inputs tested from 0 to $10^2$, $10^3$, and $10^5$ copies/test in the presence of the splitting probes without visible dropping of the intensity along with the increased MRSA DNA copy input (FIG. 9, "+" cassettes #8, 6, 4, and 2). Presence of the splitting probes in the assay does not affect the amplification and detection of the nuc and mecA gene products as no visible difference of the S line and M line was detected on the cassettes at different MRSA DNA copy inputs between the assays with and without the splitting probes (FIG. 9). Inclusion of the splitting probes in the assay thus makes the C line visible at even intensity from the different MRSA DNA copy inputs tested, which can serve as an indicator of whether an inhibitor is present in the HDA reaction.

We claim:

1. A nucleic acid assay method, the method comprising:
    performing a nucleic acid amplification reaction to amplify a control nucleic acid and a test nucleic acid, wherein the performing the nucleic acid reaction generates a reaction product composition which comprises a test product comprising a first label, a test product comprising a second label, and/or a control product comprising the second label;
    contacting the reaction product composition with a lateral flow strip after the performing the nucleic acid reaction, wherein the lateral flow strip comprises a control capture zone and a test capture zone;
    wherein the control product, if present, is captured in the control capture zone; the test product comprising the first label, if present, is captured in the test capture zone, and the test product comprising the second label, if present, is captured in the control capture zone; and
    wherein successful amplification of either the control nucleic acid or the test nucleic acid provides a captured nucleic acid in the control capture zone.

2. The method of claim 1, further comprising detecting the captured control product, the captured test product comprising the first label, and/or the captured test product comprising the second label.

3. The method of claim 1, wherein the nucleic acid amplification reaction is a helicase dependent amplification (HDA) reaction.

4. The method of claim 1, wherein a first antibody is immobilized to the test capture zone and a second antibody is immobilized to the control capture zone.

5. The method of claim 4, wherein the first antibody specifically binds to the test product comprising the first label and the second antibody specifically binds to the control product comprising the second label and the test product comprising the second label.

6. The method of claim 1, wherein the test product comprising the first label is captured in the control capture zone.

7. The method of claim 6, wherein a first antibody is immobilized to the test capture and to the control capture zone and a second antibody is immobilized to the control capture zone.

8. The method of claim 7, wherein the first antibody specifically binds to the test product comprising the first label and the second antibody specifically binds to the control product comprising the second label and the test product comprising the second label.

* * * * *